United States Patent [19]

Drake et al.

[11] 4,449,981
[45] May 22, 1984

[54] GLASS ENCAPSULATED MATERIALS

[75] Inventors: Cyril F. Drake, Harlow; John R. Brocklehurst, Bishop's Stortford, both of England

[73] Assignee: ITT Industries, Inc., New York, N.Y.

[21] Appl. No.: 272,144

[22] Filed: Jun. 10, 1981

[30] Foreign Application Priority Data

Jun. 12, 1980 [GB] United Kingdom ............. 8019261
Dec. 10, 1980 [GB] United Kingdom ............. 8039566

[51] Int. Cl.³ ............................................. A61K 9/26
[52] U.S. Cl. ................................. 604/890; 604/894
[58] Field of Search ........................ 128/213, 260; 424/19–22; 604/890–894; 222/1, 575

[56] References Cited

U.S. PATENT DOCUMENTS 3,938,515  2/1976  Leeper et al. .................... 128/260
4,142,526  3/1979  Zaffaroni et al. ................ 604/894
4,218,255  8/1980  Bajpai et al. .................... 128/260
4,322,398  3/1982  Reiner et al. .................... 128/260

Primary Examiner—Benjamin R. Padgett
Assistant Examiner—T. J. Wallen
Attorney, Agent, or Firm—James B. Raden; Harold J. Holt

[57] ABSTRACT

A device for the controlled release of an active material into a liquid medium comprises a liquid soluble body having an array of cavities therein containing the active material. The body may be enclosed in a casing of a material having a relatively low dissolution rate and provided with means, e.g. an aperture whereby a portion of the body can be exposed to dissolving attack by the liquid medium. The body is so constructed that the cavity contents are released sequentially and at a predetermined rate.

13 Claims, 8 Drawing Figures

GLASS ENCAPSULATED MATERIALS

This invention relates to arrangements adapted to release controlled quantities of a substance into an aqueous medium over an extended period of time.

A constant problem in the medical field and in particular in the field of veterinary medicine, is that of supplying a patient over an extended period of time with a series of accurately measured doses of a medicament. Treatment with medicaments of an inorganic nature can be effected by incorporating the inorganic material in a water soluble glass and then implanting a small pellet made from the glass into the body of the patient whereby the active material is released at a predetermined rate into the body fluids. Such techniques are described in our U.S. Pat. No. 4,283,227 and co-pending British applications Nos. 49600/78, and 8025964. The glass compsitions described in these applications are designed to release one or more active materials into a liquid environment. Typically such glasses comprise a glass-forming oxide together with one or more glass-modifying oxides, the ratio of the former to the latter and the proportions and nature of the constituents being selected so as to provide the glass with a desired rate of dissolution in water. The materials to be released are incorporated in the glass, generally in oxide form. Such materials are restricted to those which have a reasonable stability at the glass forming temperatures. In particular, organic materials cannot be incorporated in the glass in this way.

Whilst such a device provides for the release of an organic material from a soluble glass structure, the relatively large size and small number of the cavities results in a release rate/time profile that comprises a series of pulse doses. There are many applications where this pulsed release of active materials may be undersirable.

The object of the present invention is to provide a water soluble device for the release of an active material at a predetermined and substantially continuous rate.

According to one aspect of the present invention there is provided a device for the controlled release over a predetermined period of an active material into a liquid medium, characterised in that the device comprises a water soluble body having a plurality of cavities therein and within which the active material is contained such that the active material will be released at a predetermined rate as the body dissolves.

According to another aspect of the present invention there is provided a device for the controlled release over a predetermined period of an active material into a liquid medium, characterised in that the device comprises a casing containing a water soluble material having a plurality of cavities containing the active material, and that the casing has at least one access port whereby the liquid can contact the water soluble material so as to release the active material from the cavities through the port.

According to a further aspect of the invention there is provided a device for the controlled release of an active material into a liquid medium over a predetermined period, the device including a body formed of one or more liquid soluble materials and surrounded by a casing of a material having a relatively low dissolution rate, characterised in that said body has a plurality of cavities for containing the active material, that said casing has an access port, or a region that readily dissolves to provide an access port, whereby a portion of the body is exposed to dissolving action by the liquid, and that the body is so constructed that it is dissolved by the liquid to release in a sequential manner the active material contained in the cavities.

A particularly desirable feature of the device is its ability to provide a predetermined time profile of the release rate of the active material. This is important e.g. where measured quantities of a drug are to be supplied to a patient over a period of weeks or days from a liquid soluble body implanted in the body of the patient. Furthermore this release rate can be substantially continuous.

In a preferred embodiment of the invention the device is enclosed in a relatively low solubility casing having an opening whereby dissolution of the body with consequent release of the cavity contents can be effected.

We have found that an encapsulent or casing of a material having a relatively low dissolution rate supports the assembly of cavities whilst dissolution is taking place and provides the additional function of sealing the ends of the capillaries. After dissolution of the said assembly is completed the casing itself slowly dissolves or biodegrades so that there is ultimately no solide residue. We have also found that by arranging tubes having different dissolution rates in a variety of geometric configurations it is possible to provide for different predetermined time/release rate profiles of the active material. In many applications, e.g. where certain drugs are to be released into the body fluid of a human or non-human animal, a substantially continuous release rate is highly advantageous.

A number of materials may be employed to form the body, but we prefer to use a water soluble glass composition. The cavities may be provided by an array of capillaries formed in the glass.

Embodiments of the invention will now be described with reference to the accompanying drawings in which.

Figure 1:
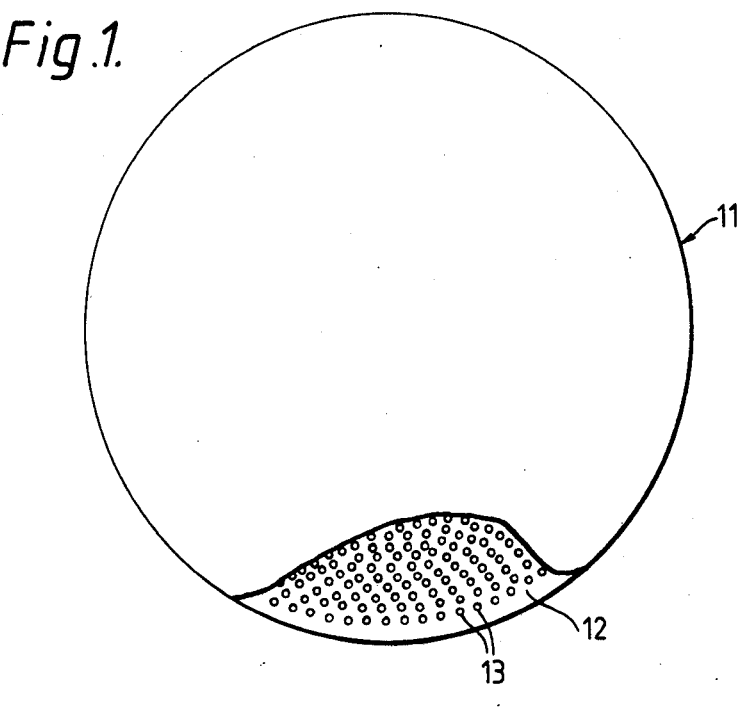
FIG. 1 is a cut-away plan view of the water soluble body.
Figure 2:
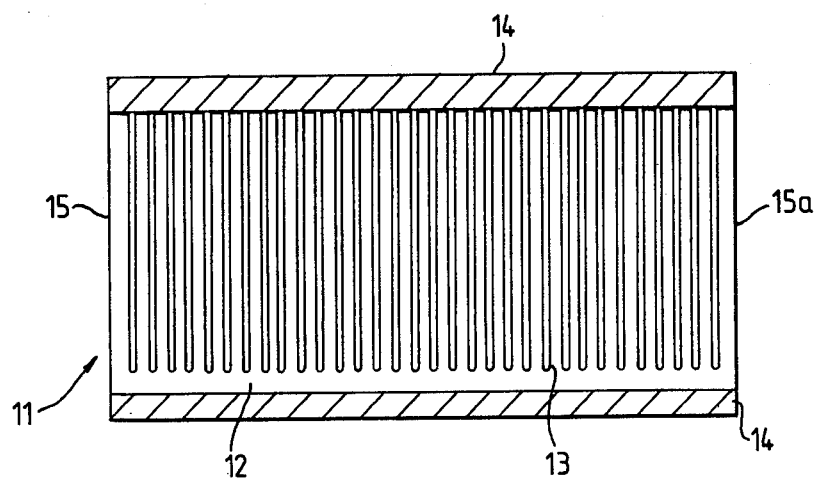
FIG. 2 is a cross-section of the body of FIG. 1.

Referring to FIGS. 1 and 2, the water-soluble body, which advantageously is made of a water-soluble glass, is shown in plan view and cross section respectively. The body 11 comprises a solid matrix 12 in which an array of microtubular cavities or capillaries 13 is provided. The capillaries 13 are filled each with the same or with different active materials and are closed by a seal 14 which should be made of a material of lower rate of water dissolution than that of the matrix 12. Alternatively the thickness of the seal 14 may be such that although its rate of solution is comparable to that of the material of the body 12, the body dissolves from the lateral faces befores the seal 14 has been completely dissolved.

When immersed in an aqueous medium the body 11 slowly dissolves from the faces 15, 15a (FIG. 2) such that the capillaries 13 are successively opened and can thus release their contents into the aqueous medium. Typically the aqueous medium is the body fluid of an animal and the active material comprises a medicament which is thereby released at a controlled rate into the animals body fluids.

To prevent premature discharge of the active material it is essential that the cover plate 14 and the fusion sealed ends of the capillaries are dissolved at a slower rate than that of the glass matrix. This may be achieved by various techniques. For example the cover plate may be made of a glass of lower solubility than the bulk material of the body, a similar plate being applied to the other face of the body to prevent attack of the fusion sealed capillary ends. Alternatively the cover plate 14 may be of the same composition as the body, the top and bottom faces of the body being protected by a layer (not shown) of a substantially insoluble wax material.

Other methods of sealing the cavities include plasma spraying of a glass or a metal, or moulding of a polymeric material layer to the body.

Figure 3:
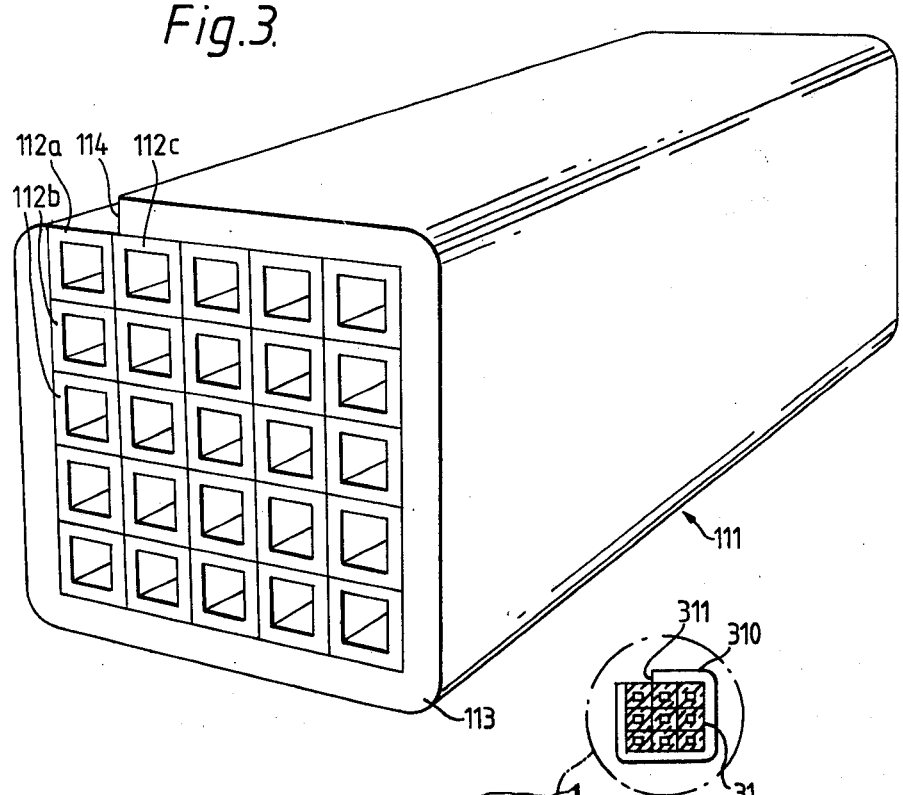
FIG. 3 is a schematic view of an alternative form of liquid soluble body.

Referring now to FIG. 3, the liquid soluble body 111 comprises an array of soluble capillary tubes 112 enclosed in a low solubility casing 113. The tubes 112 may be made of water soluble glass compositions or from other water soluble material such as biodegradable polymers. The outer casing 113 or the body 111 may also be made from a water soluble glass or from a biodegradable polymer or wax. An elongate opening is provided in the casing 113 whereby one tube 112a of the array is exposed to dissolving attack by the liquid medium in which the body 111, when in use, is immersed. This elongated opening may be filled with high solubility material.

The tubes 112 are disposed in an array, e.g. an m×m square array, and are made of soluble materials of such a nature that the tubes 112b have a dissolution rate in the liquid medium that is m times that of the tubes forming the remainder of the array. It should be noted that although the tubes 112 are shown separate they will, in most applications, be fused together to form a single body. When such a body is immersed in the liquid medium the exposed tube 112a is dissolved releasing its contents and exposing the next tube 112b of the column and the relatively low dissolution rate material of the tube 112c in the adjacent column. Dissolution of the tubes 112b of the high dissolution rate column proceeds on a regular basis until that column has fully dissolves and has released its active material periodically until the last tube of the array has dissolved. The casing 113 is made of a material of a dissolution rate lower than that of any of the tubes 112 so that it is not dissolved until dissolution of the tubes has been completed.

The geometric structure of the body 111 is not of course limited to a square array of capillary tubes. Other configurations may be employed and the dissolution rates of the various tubes 112 forming the array may be provided to give a devised time/release rate profile.

The material released from the cavities of the devices or bodies of FIGS. 1, 2 and 3 may be solid, liquid or gas, and the cavities may be filled by capillary suction, vacuum filling. All the capillaries can be filled with the same material or there may be two or more materials distributed in a particular way amongst the cavities.

The cavities may contain a variety of materials to be released into an aqueous medium. Thus, in addition to drugs, hormones or other curative materials the water soluble body may also be used to release fungicides, algicides, nematocides, bacteriocides, molluscides, spermicides or mixtures thereof. Other applications include the release of an attractant for a species which it is intended to destroy. Thus, e.g. in the treatment of water courses for the prevention of bilharzia, a snail attractant can be released to attract the snails to a molluscide which is released simultaneously or in conjunction with the attractant. In a further application two materials may be released together, the materials reacting in situ to form a compound with a short half-life and which therefore cannot be readily applied by conventional means.

Figure 4:
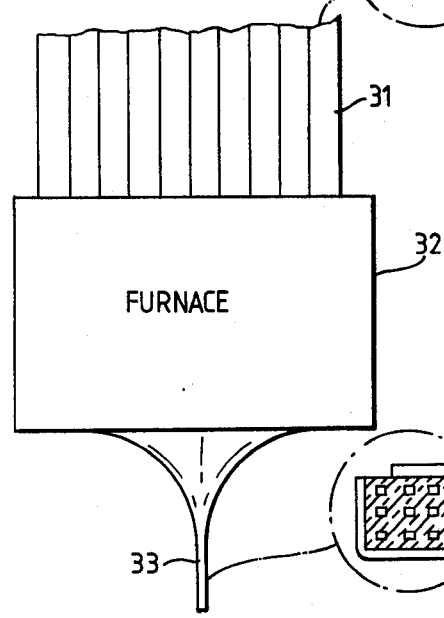
FIG. 4 is a schematic diagram of an apparatus used in the manufacture of the bodies of FIGS. 1, 2, 3 and 5 and FIGS. 5a to 5d show various further forms of liquid soluble bodies.

Referring now to FIG. 4, this shows one example of an apparatus for manufacturing the water soluble bodies of FIGS. 1, 2, 3 and 5. The bodies are prepared by a technique somewhat analogous to the manufacture of channel plates for image-intensifier tubes.

The bodies may be formed from a plurality of glass capillaries that are provided by drawing down a bundle of glass tubes 31, typically of square cross-section, which may be enclosed in a folded sheet cladding 310 and passed under tension through a furnace 32 so as to form a relatively thin multibore clad rod or fibre 33. The cladding 310 has an open longitudinal channel 311 which remains as an opening when the assembly is drawn down. The drawn assembly is then sawn into sections each comprising a bundle of substantially parallel capillaries 35 fused together to form a pellet like body. The tube assembly is then filled with the active material and end plates (not shown) are applied to seal the tube.

Figure 5A:
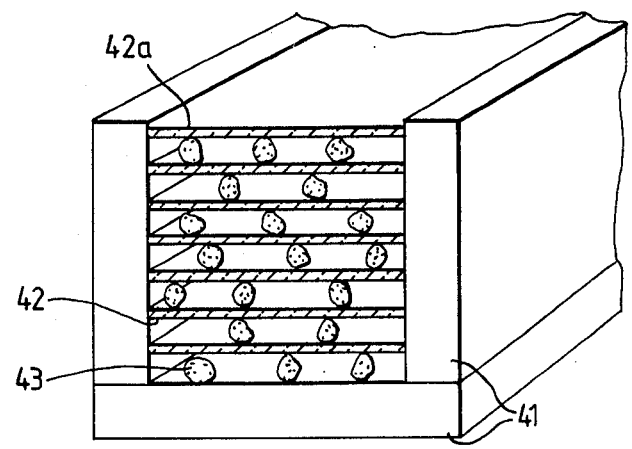

Further forms of liquid soluble body are shown in FIGS. 5a to 5d. In each case the body may be assembled as a preform comprising liquid soluble glass components, the preform then being drawn down and sectioned to provide the bodies. The capillary cavities in the bodies are defined by a series of spaced plate members. Referring now to FIG. 5a the liquid soluble body shown therein comprises a substantially U-shaped trough formed by an assembly of three plate members 41 of a material of a relatively low dissolution rate. The space within the trough is occupied by a stack of soluble plates 42, these plates being separated by powder particles 43 so as to define a series of parallel sided capillary cavities. The open ends of the cavities are sealed by end plates (not shown).

When such a body is immersed in the liquid medium dissolution of the outermost plate 42a takes place releasing the contents of the corresponding cavity and exposing the next plate to dissolving attack. In this way the cavities are exposed in a periodic manner.

Figure 5B:
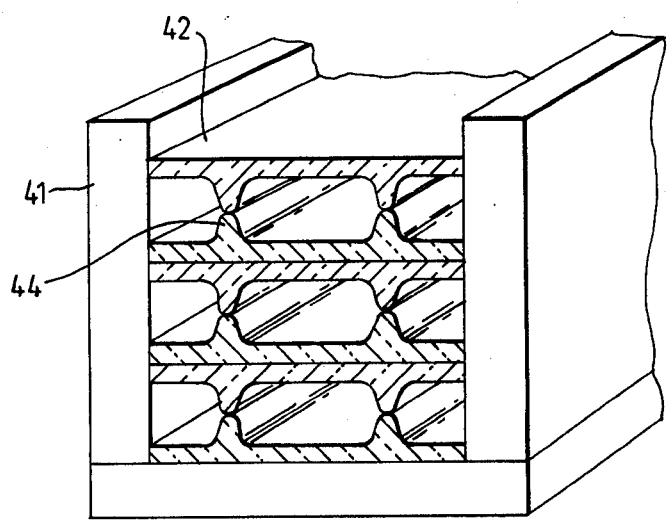
Figure 5C:
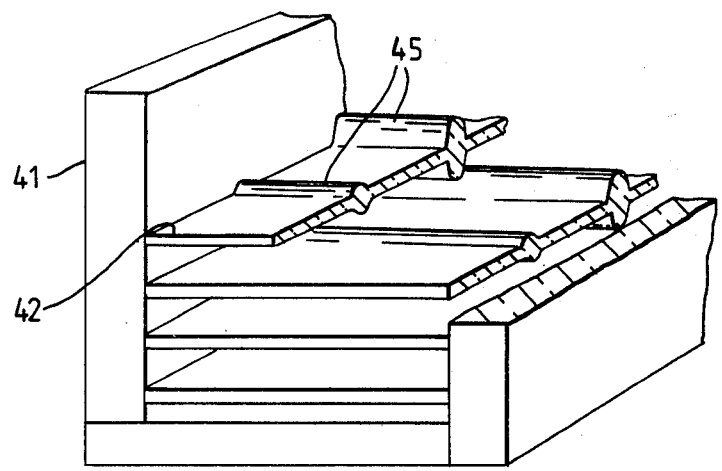

FIG. 5b shows an arrangement in which the plates 42 have longitudinal ridges 44 to define the separation between the plates. In an alternative arrangement (FIG. 5c) the plates 42 are provided with transverse ridges 45. Such ridges can be produced by passing the softened plate material through a pair of suitably indented rollers. In some applications the plates 42 may be provided with alternate large and small transverse ridges. The drawn assembly can then be sectioned through the large ridges which thus provide sealing of one end of each cavity. The small ridges reduce the opening at the other ends of the cavities.

Figure 5D:
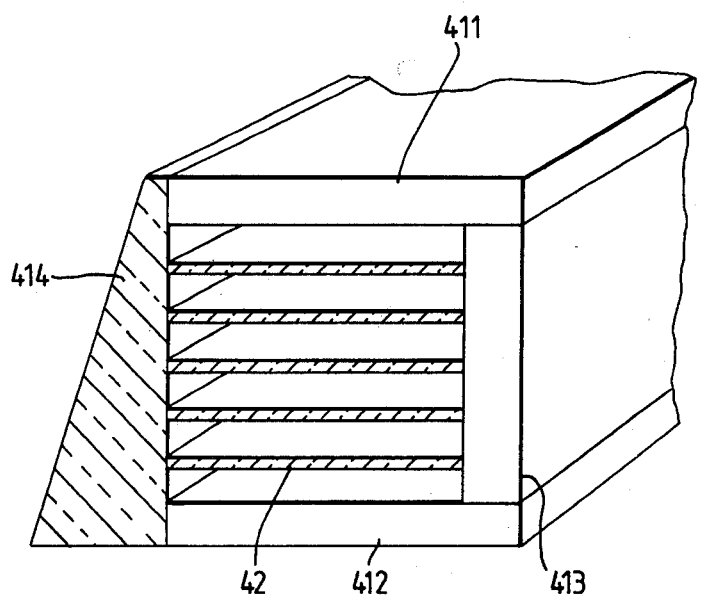

FIG. 5d illustrates a further technique for providing a predetermined release rate of the contents of the cavities. In this arrangement the top 411, bottom 412 and one side 41 of the body are sealed with a low solubility material. The remaining side is sealed with a strip 414 of soluble material having a trapezoidal cross section. When this body is immersed in the liquid medium the thinnest portion of the strip 414 dissolves first exposing the uppermost cavity. As the thicker portions of the strip 414 dissolve successive cavities are exposed.

The water soluble bodies or pellets described herein may be used in a variety of applications. Typically they may be employed in the form of subcutaneous implants of the controlled suply of a drug, medicament or curative material to a human or non-human animal. To implant the pellet in an animal it is conveniently inserted with the aid of a hypodermic gun into or adjacent the ear lobe where it is thus in contact with the body fluids, the material contained in the pellet being transported from the implantation site by the animal's body fluids. Where poultry are to be treated the pellet may be administered orally as it will then lodge in the gizzard, the active material being released into the intestine and from there, via the intestinal wall, to the bloodstream. Similarly, a pellet may be administered orally in the form of a bolus to ruminant animals for lodgement in the rumen. Such techniques of administration will of course be apparent to those skilled in veterinary medicine.

As previously stated it is preferred to form the body or pellet from a water soluble glass. For this purpose the glass must be workable, i.e. it must be drawable into tube and fibres, it must have a suitable solubility for the particular application, and, where the pellet or body is to be administered to an animal, it must be non-toxic and produce a minimal reaction at the site of implantation. Furthermore, where such a body is administered to an animal that is subsequently slaughtered for meat, the glass must not contain elements that could be undesirable or even harmful for human consumption.

We have found that glasses based on the $Na_2O$ $(K_2O):CaO:P_2O_5$ system are suitable for such applications. These glasses contain no harmful or toxic elements and are readily workable. The glass solubility can be controlled by adjusting the ratio of the glass-former to glass-modifiers and the relative proportions of the alkali metal oxide and the calcium oxide constituents relative to the glass forming oxide. In general an increase in the proportion of calcium oxide produces a decrease in solubility and vice versa. In some applications some or all of the calcium oxide may be replaced by magnesium oxide, which has a more marked effect of reducing the dissolution rate of the glass. The incorporation of zinc oxide (ZnO) has a less marked effect on the dissolution rate. In some applications a small proportion of alumina or ferric oxide $TiO_2$ may be added to the glass to further reduce its water dissolution rate. The technique of controlling the dissolution rate of a glass is more fully described in our published British specification No. 1 512 637 (U.S. Pat. No. 4,123,248) and in our co-pending British application No. 7930041 (U.S. Pat. No. 4,350,675). It will be apparent that other glass modifying metal oxides and/or glass forming oxides such as boric acid, silica or a alumina may be incorporated in the glass depending on the particular application envisaged.

To illustrate the typical glass compositions that may be employed, a series of glass compositions within the following composition range, which is by no means limiting, was prepared. The composition range is listed in Table I.

TABLE I

| Glass constituent | Proportion Range, Mole % |
|---|---|
| $Na_2O$ | 0–50 |
| $K_2O$ | 0–50 |
| CaO | 0–30 |
| ZnO | 0–30 |
| MgO | 0–30 |
| $P_2O_5$ | 29–70 |

It should be noted that although each constituent is expressed in the form of its oxide it is not necessarily present in this form in the glass composition. The glasses can be prepared from the oxide constituents, but in the present case the glass constituents were as follows:

| | |
|---|---|
| $NaH_2PO_4$ | Sodium dihydrogen phosphate |
| $KH_2PO_4$ | Potassium dihydrogen phosphate |
| $CaCO_3$ | Calcium carbonate |
| $Ca(H_2PO_4)_2$ | Calcium dihydrogen phosphate |
| $ZnCO_3$ | Zinc carbonate |
| $MgCO_3$ | Magnesium carbonate |
| $P_2O_5$ | Phosphorus pentoxide |

These glasses were prepared by mixing weighed quantities of the batch constituents followed by fusion at 100° to 1100° C. in a platinum crucible to form a homogeneous glass. As some phosphorus pentoxide is always lost by evaporation the composition of the finished glass was determined in each case by chemical analysis.

It will be appreciated by those skilled in the art that the carbonates and phosphates in the above list of constituents decompose at the fusion temperature to release the corresponding oxides. It will also be apparent that other suitable oxide precursors include thermally unstable nitrates, hydroxides, citrates and acetates, ammonium phosphate and phosphoric acid. The formation of glasses from such oxide precursor materials is well known in the glass-making art.

A major application of the liquid soluble body is the controlled delivery of organic compounds to animals, the body being administered for example, as an implant which is thus in contact with the interstitial fluid of the animal. Hence the dissolution rate of each glass composition in an interstitial fluid was examined. Weighed quantities of each glass were placed in the fluid at a temperature of 38° C. and in a 3% by volume $CO_2$ atmosphere and the glass weight loss was periodically determined. The model interstitial fluid employed had the following composition:

| | |
|---|---|
| $NaHCO_3$ | 2.52 gm |
| NaCl | 5.85 gm |
| $MgSO_47H_2O$ | 0.37 gm |
| $K_2HPO_4$ | 0.435 gm in 1 liter of solution. |
| $CaCl_26H_2O$ | 0.545 gm |
| Na acetate $3H_2O$ | 0.816 gm |
| Bovine serum albumin | 1.0 gm. |

The results of the dissolution tests are summarised in Table II below.

TABLE II

Specific Glass Composition with Dissolution Rate in IF at 38° C.

| Glass No. | Mole % Na$_2$O | K$_2$O | CaO | ZnO | MgO | P$_2$O$_5$ | Diss. rate mgm/cm$^2$/24 hr. |
|---|---|---|---|---|---|---|---|
| 260181.2 | 33.9 | 1.0 | 0 | 10.1 | 10.1 | 45.1 | 1.0 |
| 260181.1 | 41.1 | 1.3 | 7.1 | 5.7 | 0 | 44.8 | 6.3 |
| 090580.4 | 40.6 | 1.2 | 8.4 | 0 | 7.9 | 41.9 | 7.2 |
| 160281 | 38.4 | 1.2 | 14.9 | 0 | 0 | 45.5 | 15.3 |
| 130281 | 46.8 | 1.4 | 0 | 10.5 | 0 | 41.3 | 59.8 |
| 180480.1 | 20.7 | 0 | 13.2 | 13.2 | 0 | 52.9 | 4.0* |
| 290480.12 | 34.7 | 1.0 | 14.3 | 14.3 | 0 | 35.6 | 4.8* |

*These rates were measured in IF with low HCO$_3$ and in air.

These results illustrate the feasibility of providing suitable glass compositions for the construction of the liquid soluble body.

The techniques described herein are not of course limited to the use of glass compositions. Thus, in some applications liquid soluble and/or biodegradable polymeric materials may be employed. However, glasses are to be preferred as they provide a continuously variable range of composition and dissolution rate and are not subject to catastrophic biochemical attack.

We claim:

1. A device for the controlled release of an active material into a liquid medium over a predetermined period, characterised in that the device comprises a body formed of one or more water soluble glass materials surrounded by a casing of material having a relatively low or zero disslution rate, said body having a plurality of capillary cavities for containing the active material, said casing having an access port or a region that readily dissolves to provide an access port, whereby a portion of the body is exposable to dissolving action by the liquid, the body being so constructed that it is dissolved by the liquid to release in a sequential manner the active material contained in the capillary cavities.

2. A device as claimed in claim 1 characterised in that said casing is formed of a water soluble glass having a relatively low dissolution rate.

3. A device as claimed in claim 1 characterised in that the active material includes a drug or other curative material, a hormone, an insecticide, a nematocide, a fungicide, an algicide, a bacteriocide, a molluscicide, a spermicide or mixtures thereof.

4. A device as claimed in claim 1 in the form of a subcutaneous implant or of a bolus for oral administration.

5. A device as claimed in claim 1, characterised in that the release rate of the active material has a predetermined profile over the major portion of the release period.

6. A device as claimed in claim 1 characterised in that two or more active materials are distributed in the cavities in a predetermined pattern.

7. A method of treating a human or an animal, including administering to the human or animal a device as claimed in claim 1.

8. A method as claimed in claim 7 characterised in that said device is administered in the form of a subcutaneous implant.

9. A device for the controlled release of an active material into a liquid medium over a predetermined period, the device including a m×m array of capillary tubes of a liquid soluble material and containing the active material, and an outer casing of a material having a relatively low dissolution rate and having an access port via which at least one tube of the array is exposed to dissolving action by the liquid, and wherein the array row or column of tubes including said one tube is made of a material having a dissolution rate in the liquid substantially m times that of a material from which the remainder of the tubes are made, the arrangement being such that dissolution of the tubes of the successive columns releasing the active material into the liquid medium is effected in a sequential manner.

10. A method of controlled delivery of an active material into water or other aqueous system, characterised in that the active material is encapsulated within a casing containing a solid water soluble glass material having a multiplicity of capillary cavities distributed therethrough and containing the active material, said solid being soluble in said aqueous system at a predetermined rate, said casing having a lower dissolution rate in the aqueous system than said water soluble glass material, said casing having at least one access means which readily dissolves to provide an access port whereby the aqueous system can contact said water soluble glass material so as to release in a sequential manner the contents of each capillary cavity through the access means.

11. A method as claimed in claim 10 characterised in that said casing has a relatively low dissolution rate.

12. A method as claimed in claim 11 characterised in that the capillaries are defined by an array of substantially flat parallel plates.

13. A method as claimed in claim 11 characterised in the capillaries comprise m×m array of capillary tubes.

* * * * *